(12) United States Patent
Blondel et al.

(10) Patent No.: US 11,992,280 B2
(45) Date of Patent: May 28, 2024

(54) MEDICAL ROBOT COMPRISING AUTOMATIC POSITIONING MEANS

(71) Applicant: Quantum Surgical, Montpellier (FR)

(72) Inventors: Lucien Blondel, Montpellier (FR); Frédéric Banegas, Jacou (FR); Sébastien Olive, Montpellier (FR); Fernand Badano, Lyons (FR); Bertin Nahum, Castelnau-le-Lez (FR)

(73) Assignee: Quantum Surgical, Montpellier (FR)

( * ) Notice: Subject to any disclaimer, the term of this patent is extended or adjusted under 35 U.S.C. 154(b) by 656 days.

(21) Appl. No.: 17/280,670

(22) PCT Filed: Sep. 25, 2019

(86) PCT No.: PCT/FR2019/052249
§ 371 (c)(1),
(2) Date: Mar. 26, 2021

(87) PCT Pub. No.: WO2020/065209
PCT Pub. Date: Apr. 2, 2020

(65) Prior Publication Data
US 2021/0338351 A1    Nov. 4, 2021

(30) Foreign Application Priority Data

Sep. 27, 2018   (FR) ...................................... 1858917
Mar. 1, 2019   (FR) ...................................... 1902154

(51) Int. Cl.
*B25J 5/00*        (2006.01)
*A61B 34/00*      (2016.01)
(Continued)

(52) U.S. Cl.
CPC .............. *A61B 34/32* (2016.02); *A61B 34/25* (2016.02); *A61B 34/30* (2016.02); *A61B 90/39* (2016.02);
(Continued)

(58) Field of Classification Search
CPC ......... A61B 34/32; A61B 34/25; A61B 34/30; B25J 9/162; B25J 13/089; G16H 40/63; G05D 1/2462; G05D 1/6895
See application file for complete search history.

(56) References Cited

U.S. PATENT DOCUMENTS

2010/0137880 A1    6/2010   Nahum et al.
2012/0101508 A1    4/2012   Wook Choi et al.
(Continued)

FOREIGN PATENT DOCUMENTS

CN    101217913 A    7/2008
CN    102805638 A   12/2012
(Continued)

OTHER PUBLICATIONS

International Search Report PCT/FR2019/052249, dated Dec. 6, 2019, 3 pages.

*Primary Examiner* — Ryan Rink
(74) *Attorney, Agent, or Firm* — ARENTFOX SCHIFF LLP (57) ABSTRACT

The invention relates to a medical robot (10) comprising a motorized mobile base (13), spatial-location sensors (17) secured to the mobile base, and a control unit (16) that stores in memory an intervention plan comprising at least one action to be performed on the anatomy of interest of a patient (30). The control unit is configured to: —detect, from information coming from the spatial-location sensors (17), a position of the anatomy of interest of the patient with respect to the medical robot, —identify, from the position of the anatomy of interest of the patient and from the intervention plan, at least one favourable position of the mobile base of the medical robot for which position the medical robot is capable of performing the action or actions from the intervention plan, —move the mobile base of the medical robot (Continued)

into an optimal position selected from among the favourable position or positions identified.

21 Claims, 4 Drawing Sheets

(51) Int. Cl.
  *A61B 34/30* (2016.01)
  *A61B 34/32* (2016.01)
  *A61B 90/00* (2016.01)
  *B25J 9/16* (2006.01)
  *G05B 13/04* (2006.01)
  *G16H 40/63* (2018.01)
  *A61B 34/10* (2016.01)
  *A61B 34/20* (2016.01)
  *G05D 1/246* (2024.01)
  *G05D 1/689* (2024.01)

(52) U.S. Cl.
  CPC .............. *B25J 5/007* (2013.01); *B25J 9/162* (2013.01); *G05B 13/04* (2013.01); *G16H 40/63* (2018.01); *A61B 2034/107* (2016.02); *A61B 2034/2055* (2016.02); *A61B 2090/3945* (2016.02); *G05D 1/2462* (2024.01); *G05D 1/6895* (2024.01)

(56) References Cited

U.S. PATENT DOCUMENTS

| | | | |
|---|---|---|---|
| 2015/0057675 | A1 | 2/2015 | Akeel et al. |
| 2016/0331474 | A1 | 11/2016 | Lacal et al. |
| 2018/0001475 | A1* | 1/2018 | Steinle .................. A61B 90/37 |
| 2018/0132966 | A1 | 5/2018 | Désaulniers et al. |
| 2019/0069962 | A1* | 3/2019 | Tabandeh ............... A61B 34/25 |
| 2019/0216555 | A1* | 7/2019 | DiMaio .................. B25J 9/1664 |
| 2019/0231460 | A1* | 8/2019 | DiMaio .................. B25J 9/1676 |
| 2022/0153364 | A1* | 5/2022 | Nahum .................... B60S 9/12 |

FOREIGN PATENT DOCUMENTS

| | | |
|---|---|---|
| CN | 203381704 U | 1/2014 |
| CN | 105473182 A | 4/2016 |
| CN | 107334598 A | 11/2017 |
| CN | 107753108 A | 3/2018 |
| FR | 3043970 A1 | 5/2017 |
| JP | 2017046966 A | 3/2017 |
| WO | 2017076886 A1 | 5/2017 |
| WO | 2017147596 A1 | 8/2017 |
| WO | 2018052796 A1 | 3/2018 |

* cited by examiner

MEDICAL ROBOT COMPRISING AUTOMATIC POSITIONING MEANS

CROSS-REFERENCE TO RELATED APPLICATIONS

This application is a National Phase of PCT/FR2019/052249, filed on Sep. 25, 2019, which claims priorities to French Patent Application No. 1858917, filed on Sep. 27, 2018, and French Patent Application No. 1902154, filed on Mar. 1, 2019, the disclosures of which are hereby incorporated by reference in their entireties.

TECHNICAL FIELD

The present invention lies in the field of medical robots intended to assist a practitioner during a medical treatment. The invention concerns in particular a medical robot including means for automatic positioning in a treatment room as well as a method for automatic positioning of a medical robot.

PRIOR ART

Many medical treatments necessitate very precise positioning or movement of a medical tool relative to an anatomy of interest of a patient.

For example, some medical treatments necessitate placing a high-intensity focused ultrasound generator in contact with the skin of the patient or inside the patient to destroy a tumour.

According to another example, in neurosurgery, some medical treatments necessitate introduction of a catheter, a needle or an electrode into a target zone to diagnose or treat various pathologies.

According to a further example, in orthopaedic surgery, the practitioner frequently has to position a drill, a milling device or some other instrument to modify a bone surface with the aim of reducing fractures, correcting a deformity or alleviating bone degeneration.

For some treatments described above there exist at present medical robots enabling a practitioner to place, hold or guide a medical tool.

A medical robot of this kind generally executes a treatment plan including one or more actions to be effected on an anatomy of interest of a patient.

A treatment plan of this kind is generally determined during a planning phase preceding the medical treatment, after which it is transmitted to the medical robot which stores it for example in the memory of a control unit integrated into the medical robot and configured to control the medical robot.

The planning phase may be based on medical images of scanner, tomodensitometry, magnetic resonance imaging (MRI), positron emission tomography (PET), ultrasound, X-ray, etc type. The practitioner is then able to choose a position or a trajectory of the medical tool relative to an anatomy of interest of the patient in one or more medical images.

In some cases the planning phase is based on a 3D (three-dimensional) representation of the anatomy of interest acquired by a non-medical image acquisition system or by constructing a geometrical model of the anatomy of interest on the basis of points or surfaces collected on said anatomy of interest.

The medical robot must be positioned at a specific location in a treatment room, beside the table on which is placed the patient for whom the medical treatment is intended, so that the medical robot is able to execute one or more actions from the treatment plan. The medical robot carries a tool, for example a medical instrument guide or a medical instrument mounted at one end of an articulated arm, and the position of the medical robot must be such that the articulated arm is able to position or move the tool in accordance with all the intended positions or trajectories in the treatment plan. In fact, if this were not the case, repositioning the patient or the robot in the treatment room when all the operators and the equipment have to be sterile could prove particularly labour-intensive and involve a significant loss of time.

Positioning the medical robot is therefore particularly important for it to be possible for the actions from the treatment plan to be executed in a precise manner.

In most cases positioning the medical robot is a manual operation which relies on the training and the experience of the operator, which can lead to positioning errors or to non-optimum positions of the medical robot.

In some cases the medical robot is positioned in an automatic manner at an optimum position for executing the treatment plan. In the international patent application WO2017/147596 in particular the medical robot may be positioned in an optimum position with the aid of an external tracking system including optical sensors configured to detect the position of markers placed on elements of the treatment room and on the medical robot. The position of the medical robot can then be defined relative to those markers. The tracking system is for example disposed in a surgical lamp, a mobile support, the walls or the ceiling of the treatment room. Precise determination of the optimum position of the medical robot is then conditioned by the correct positioning of the tracking system and the various markers. The tracking system and the various markers being installed by an operator, there are risks of errors in the optimum position of the medical robot. Also, a mapping of the treatment room is used by the tracking system to direct the medical robot and it must be certain that the arrangement of the treatment room continues to conform to that mapping or that the mapping be updated if the arrangement of the treatment room changes. Furthermore, the medical robot can be used only in a treatment room specifically prepared and mapped for the tracking system to be able to control the medical robot.

The need for a reliable system that is easy to install and to maintain therefore continues to exist for positioning a medical robot at an optimum position in a treatment room in order for the medical robot to be able to execute with precision various actions from a treatment plan on an anatomy of interest of a patient.

SUMMARY OF THE INVENTION

An objective of the present invention is to remedy some or all of the disadvantages of the prior art, in particular those described above, by proposing a solution enabling a medical robot to be positioned autonomously at an optimum position in any treatment room so as to be able to execute various actions from a treatment plan on a patient placed on a table in said treatment room. By "any treatment room" is meant that said room is not specifically prepared for the medical robot to function in that room and that the medical robot has no a priori mapping of the room or information relating to the arrangement of the room before the commencement of the process of positioning the medical robot in the treatment room.

To this end, and in accordance with a first aspect, the present invention proposes a method for automatic positioning of a medical robot to carry out a medical treatment on a patient. The medical robot includes a motorized mobile base enabling movement of the medical robot and a control unit storing a treatment plan including at least one action to be effected on an anatomy of interest of said patient. The positioning method includes the following steps executed autonomously by the medical robot:

- detection of the position of the anatomy of interest of the patient relative to a position of the medical robot,
- identification on the basis of the position of the anatomy of interest of the patient and of the treatment plan of at least one favourable position of the mobile base of the medical robot at which the medical robot is capable of effecting said at least one action from the treatment plan,
- movement of the mobile base of the medical robot to an optimum position selected from the identified favourable position or positions.

In the present application the term "medical" is to be understood in a broad sense and may concern equally well a non-surgical context and a surgical context.

A medical robot of this kind may for example include an articulated arm with a plurality of degrees of freedom at the end of which may be mounted a tool, for example a medical instrument guide or a medical instrument, such as an ultrasound generator, a catheter guide, a needle, an electrode, a probe, a bistoury, a drill, etc.

According to another example, a medical robot of this kind may be used for example to produce medical images (scanner, MRI, X-ray, etc.). In a case of this kind the medical robot may for example include a medical imaging device mounted on a support.

The arm or the support on which the tool (medical instrument guide, medical instrument or medical imaging device) is mounted is fastened to the motorized mobile base of the medical robot.

The medical robot is configured to identify autonomously at least one favourable position of the mobile base of the medical robot at which the medical robot could execute each action from a treatment plan.

A favourable position of the mobile base of the medical robot is determined as a function of the position of the anatomy of interest of the patient, of the treatment plan, and possibly of the position of a table in a treatment room on which the patient is placed.

The positions of the medical robot, of the table, of the anatomy of interest of the patient, and possibly of other elements of the treatment room are defined in the same spatial frame of reference. These positions are for example detected by the medical robot by spatial location means such as video cameras, rangefinders, inertial, optical or odometric sensors, etc. These spatial location means are carried by the medical robot, that is to say fastened to the mobile base of the medical robot.

It should be noted that in the prior art the position of the anatomy of interest is sometimes known a priori relative to a frame of reference of the treatment room. A simple change of frame of reference of this known position in a frame of reference of the medical robot is not a "detection" of the position of interest within the meaning of the invention. In the invention, the position of the anatomy of interest of the patient is not known a priori. It is completely detected by the medical robot during the method of the invention.

By "anatomy of interest" of the patient is meant at least a part of the human body of the patient for which the treatment plan provides a treatment.

A treatment plan includes one or more actions to be carried out on the anatomy of interest of the patient. One action from the treatment plan corresponds for example to being able to manipulate a tool in a predetermined volume, to place a treatment tool in a predetermined position or to move that tool in accordance with a predetermined trajectory relative to the anatomy of interest of the patient. According to another example, one action from the treatment plan may equally consist in having the tool execute a particular operation, such as for example starting up an ultrasound generator or modifying the intensity of emission of ultrasound, or triggering the capture of a medical image. These examples are not exhaustive and other types of action can obviously be envisaged. One action from the treatment plan is an action that the medical robot will have to execute during the treatment, following on from the process of automatically positioning the medical robot at an optimum position. Execution of the actions from the treatment plan is therefore not part of the method for automatic positioning of the medical robot.

It is understood that a step of the method of positioning the medical robot is executed autonomously by the medical robot when it is executed by the medical robot, and it alone, without assistance from another device or human operator. This means in particular that the information from sensors used to identify the favourable position or positions is furnished exclusively by sensors carried by the medical robot.

To implement the positioning method, the medical robot does not need to have a mapping of the treatment room or specific information on the layout of the treatment room before the positioning process commences.

All of these features enable automatic and precise positioning of the medical robot relative to the anatomy of interest to be treated so that the medical treatment proceeds in the best possible manner. The method for automatic positioning of a medical robot is therefore facilitated and made reliable.

Automatic positioning is facilitated in particular because there is no need to use or to maintain an additional device, such as for example a tracking system that assists controlling and positioning the robot.

Automatic positioning is made reliable in particular because the method according to the invention for automatic positioning of the medical robot limits the risks of error linked for example to intervention by a human operator or installation of an additional device necessary for controlling the medical robot.

The optimum position of the medical robot is determined with the aid of information from sensors fastened to the mobile base of the medical robot and not from sensors external to the medical robot. Calibration of the sensors is therefore facilitated and made reliable.

The optimum position of the mobile base of the medical robot is that enabling the most appropriate treatment of the anatomy of interest by the medical robot. The optimum position of the medical robot cannot always be defined in advance because the real position of the patient at the time of treatment does not necessarily correspond to a planned position or a position modelled during the phase of planning the treatment. It is therefore advantageous that the robot is able to be positioned automatically as a function of the position of the anatomy of interest of the patient at the very moment of the treatment, that is to say when the patient is placed on the treatment table and ready to undergo the treatment provided in the treatment plan.

The automatic positioning method according to the invention is also advantageous because the medical robot is able to function in any treatment room in that there is no need to prepare the treatment room specifically for the medical robot to be able to function therein. In fact, the medical robot does not need specific information on the treatment room and in particular does not have to store a mapping of the treatment room before the commencement of the positioning process.

As there is no need to furnish the medical robot with a mapping of the treatment room there is no need to retain any such mapping. In particular, there is no need to update a mapping of this kind if the arrangement of the treatment room changes. This therefore reduces the maintenance tasks relating to medical treatments assisted by a medical robot. This also makes it possible to limit the risks of errors linked for example to inadvertent movement of certain elements (for example markers) of the treatment room that could have been mapped and the position of which would no longer correspond exactly to the position indicated by the mapping furnished to the medical robot.

Also, with the automatic positioning method according to the invention, the same medical robot may function in any treatment room. This then limits the costs relating to medical treatments assisted by a robot because there is no need to associate a medical robot with each treatment room or to prepare a treatment room specifically for a medical robot to be functional therein.

In particular embodiments, the invention may further have one or more of the following features, separately or in all technically possible combinations.

In particular embodiments, the patient is installed on a table of a treatment room and the method includes detection of the position of the table. The identification of at least one favourable position of the mobile base of the medical robot is furthermore effected on the basis of the position of the table.

In particular embodiments, the detection of the position of the table and the detection of the anatomy of interest of the patient are effected on the basis of information from spatial location sensors carried by the medical robot.

A table of this kind is in fact an element that can be identified by the medical robot, for example using a shape recognition algorithm executed by the control unit of the medical robot.

In particular embodiments, the robot initially has no mapping of the treatment room.

In particular embodiments, the method further includes the following steps executed autonomously by the medical robot:
  generation of a mapping of the treatment room on which are represented a position of the medical robot, the position of the table, the position of the anatomy of interest of the patient, and the optimum position,
  determination on the basis of said mapping of a path of the medical robot to reach said optimum position.

In particular embodiments:
  the medical robot includes an articulated arm and a tool mounted at one end of said arm, one or more articulations of said arm being controlled by the control unit of the medical robot to position the arm in accordance with one possible configuration,
  a favourable position corresponds to a position of the mobile base of the medical robot at which there exists for each action from the treatment plan at least one possible configuration of the articulated arm enabling said action to be effected,
  the method includes calculation for each action from the treatment plan and for each identified favourable position of an accessibility parameter as a function of a number of possible configurations of the articulated arm for effecting said action when the mobile base of the medical robot is positioned at said favourable position,
  the optimum position is selected as a function of the accessibility parameters of the identified favourable positions.

It is then possible for example to select the optimum position as being that for which the accessibility parameter for a particular action from the action plan has the greatest value.

In particular embodiments, the accessibility parameter is furthermore calculated as a function of available relative movements of the articulations of the arm for each of said possible configurations of the arm.

In particular embodiments:
  the method further includes calculation for each identified favourable position of a global level of accessibility of the treatment plan, said global level of accessibility being calculated as a function of the accessibility parameters of each action from the treatment plan when the mobile base of the medical robot is positioned at said favourable position,
  the optimum position is selected as a function of the global levels of accessibility calculated for the identified favourable positions.

It is then possible to define the optimum position of the mobile base of the medical robot as being that which has the greatest value of the overall level of accessibility of the various identified favourable positions.

The global level of accessibility for an identified favourable position may for example be defined as being the sum of the accessibility parameters of each action from the treatment plan when the mobile base of the medical robot is positioned at said favourable position. The overall level of accessibility may also be defined with accessibility parameters weighted as a function of the importance of an action relative to other actions from the treatment plan.

Features of this kind enable greater flexibility during the treatment. In fact the practitioner could potentially choose during the treatment, once the robot has been positioned at the optimum position, between possible configurations for effecting such or such an action from the treatment plan. The preference for one particular configuration over another could depend on how the treatment is proceeding.

In particular embodiments, one action from the treatment plan corresponds to enabling the movement of the tool in a predetermined volume relative to said anatomy of interest of the patient.

In particular embodiments, one action from the treatment plan corresponds to enabling the movement of the tool with a predetermined trajectory relative to said anatomy of interest of the patient.

In particular embodiments, one action from the treatment plan corresponds to placing the tool in a predetermined position relative to said anatomy of interest of the patient.

In particular embodiments, at least two different favourable positions are identified and the method comprises the following steps:
  verifying a stability criterion of the mobile base of the medical robot in the selected optimum position, if said verification is positive, immobilizing the mobile base of the medical robot in said optimum position, if said verification is negative, moving the mobile base of the medical robot to another position selected from the favourable positions.

In particular embodiments, the medical robot comprises retractable feet intended to be lowered to immobilize the mobile base of the medical robot, each foot comprising a sensor making it possible to measure a local flatness defect of the floor facing said foot, and the verification of a stability criterion comprises, for each foot, a comparison of the measurement of the local flatness defect of the floor for said foot with a predetermined threshold.

In particular embodiments, the medical robot comprises retractable feet intended to be lowered to immobilize the mobile base of the medical robot, each foot comprising a sensor making it possible to measure a weight supported by said foot, and the verification of a stability criterion comprises, for each foot, a comparison of the measurement of the weight supported by said foot with a predetermined threshold.

In particular embodiments, the optimum position is selected as a function of preferences of an operator stored in the control unit.

Features of this kind make it possible to adapt the position of the medical robot to the specific requirements of a treatment or to the preferences of an operator, such as for example the intended position of the patient on the table (ventral, dorsal or lateral decubitus), a preference for installing the robot on one side of the table, the side preference of the practitioner (depending on whether the practitioner is right-handed or left-handed), etc.

In particular embodiments, the optimum position is selected by an automatic learning algorithm as a function of information extracted from an existing medical treatment database.

In particular embodiments, said automatic learning algorithm uses a multilayer neural network.

An optimum position determined on the basis of a treatment plan constructed from theoretical models taking no account of the reality of treatments already applied may be significantly different from an optimum position determined taking account of elements observed during past treatments, in particular if the theoretical modelling of the treatment plan is complicated. It is therefore advantageous to use automatic learning algorithms taking into account information relating to treatments already carried out.

In particular embodiments, the medical robot includes a user interface, the identified favourable position or positions is/are proposed to an operator via said user interface, and the optimum position is selected by said operator.

In accordance with a second aspect, the present invention concerns a medical robot including a motorized mobile base, spatial location sensors, and a control unit storing a treatment plan including at least one action to be carried out on an anatomy of interest of a patient. The control unit is configured:

to detect on the basis of information from the spatial location sensors a position of the anatomy of interest of the patient relative to the medical robot, to identify on the basis of the position of the anatomy of interest of the patient and of the treatment plan at least one favourable position of the mobile base of the medical robot at which the medical robot is capable of effecting said at least one action from the treatment plan, to move the mobile base of the medical robot to an optimum position selected from the identified favourable position or positions.

In particular embodiments, the invention may further have one or more of the following features separately or in all technically possible combinations.

In particular embodiments, the control unit is also configured to detect on the basis of information from the spatial location sensors a position of a table of a treatment room on which the patient is placed and to identify said favourable position or positions as a function of the position of the table.

In particular embodiments the control unit is also configured:

to generate a mapping of the treatment room on which are represented a position of the medical robot, the position of the table, the position of the anatomy of interest of the patient, and the optimum position, to determine on the basis of said mapping a path of the medical robot to reach said optimum position.

In particular embodiments, the medical robot furthermore includes sensors to aid detection of the anatomy of interest of the patient cooperating with markers positioned on said anatomy of interest.

Markers of this kind can for example generate light or electromagnetic signals enabling specific sensors to estimate a distance between the medical robot and the anatomy of interest.

In particular embodiments, the control unit identifies said at least one favourable position exclusively on the basis of the treatment plan and of information from sensors carried by the medical robot.

In particular embodiments, the medical robot includes an articulated arm and a tool mounted at one end of said arm. One or more articulations of said arm are controlled by the control unit of the medical robot to position the arm in accordance with one possible configuration. A favourable position then corresponds to a position of the mobile base of the medical robot at which there exists for each action from the treatment plan at least one possible configuration of the articulated arm for effecting said action. The control unit is furthermore configured:

to calculate for each action from the treatment plan and for each identified favourable position an accessibility parameter as a function of a number of possible configurations of the articulated arm for effecting said action when the mobile base of the medical robot is positioned at said favourable position, to select the optimum position as a function of the accessibility parameters of the identified favourable positions.

In particular embodiments, the control unit is furthermore configured:

to verify a stability criterion of the mobile base of the medical robot in the selected optimum position, if said verification is positive, to trigger an immobilization of the mobile base of the medical robot in said optimum position, if said verification is negative, to move the mobile base of the medical robot to another position selected from the favourable positions.

In particular embodiments, the medical robot comprises retractable feet intended to be lowered to immobilize the mobile base of the medical robot, each foot comprising a sensor making it possible to measure a local flatness defect of the floor facing said foot, and, in order to verify the stability criterion, the control unit compares, for each foot, the measurement of the local flatness defect of the floor for said foot with a predetermined threshold.

In particular embodiments, the medical robot comprises retractable feet intended to be lowered to immobilize the mobile base of the medical robot, each foot comprising a sensor making it possible to measure a weight supported by said foot, and, in order to verify the stability criterion, the control unit compares, for each foot, the measurement of the weight supported by said foot with a predetermined threshold.

DESCRIPTION OF THE FIGURES

The invention will be better understood on reading the following description given by way of nonlimiting example and with reference to FIGS. 1 to 5 which show.

In these figures, references identical from one figure to another designate identical or analogous elements. For clarity reasons, the elements represented are not necessarily to the same scale, unless otherwise indicated.

DETAILED DESCRIPTION OF EMBODIMENTS

Figure 1:
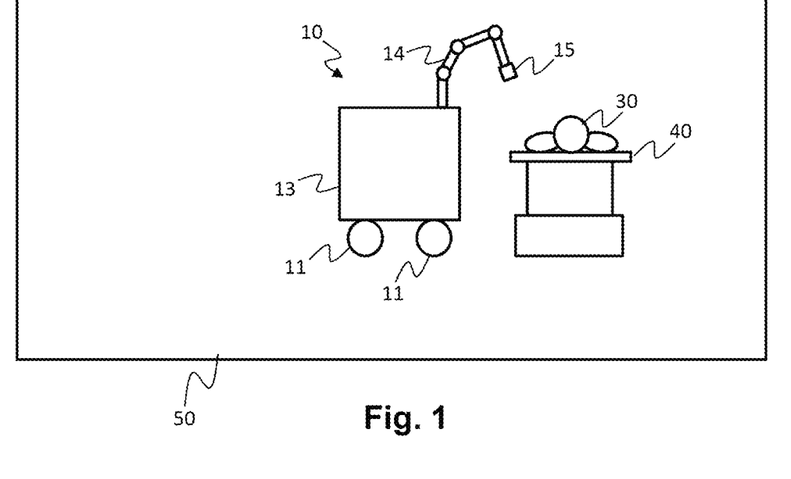
FIG. 1: a diagrammatic representation of a medical robot in a treatment room including a table on which a patient is placed.

FIG. 1 represents diagrammatically a medical robot 10 according to the invention in a treatment room 50. The treatment room 50 conventionally includes a table 40 on which a patient 30 is placed.

The medical robot 10 has a motorized mobile base 13 enabling the medical robot 10 to move. In the example considered and illustrated by way of example in FIG. 1 the mobile base 13 of the medical robot 10 is equipped with wheels 11. According to other embodiments the mobile base 13 of the medical robot 10 could be equipped with other driving means such as caterpillar tracks for example. The mobile base 13 is preferably omnidirectional, that is to say enables the medical robot 10 to move over the floor in all directions by movements in translation and/or rotation.

In the example considered and illustrated in FIG. 1 the medical robot 10 includes an articulated arm 14 at the end of which a tool 15 can be mounted. A medical robot 10 of this kind can then be used to assist a practitioner to position, to hold or to guide the tool 15.

The articulated arm 14 preferably has at least six degrees of freedom to be able to position and/or to move the tool 15 in space. However, there is nothing to prevent the arm having a different number of degrees of freedom.

For example, the tool 15 may be a high-intensity focused ultrasound generator that has to be positioned in contact with the skin or with the interior of the patient 30 to destroy a tumour.

According to another example, the tool 15 may be a guide for implanting an instrument such as a catheter, an electrode or a needle in a target zone of the patient 30.

For some minimally invasive or transcutaneous treatments the tool 15 may be a medical instrument, a probe or an electrode that has to be introduced very accurately into a target organ to enable a biopsy, resection or ablation of a portion of the anatomy of the patient 30.

According to a further example, the tool 15 may be a medical image acquisition device. In particular embodiments a device of this kind may be mounted on a support fastened to the mobile base 13 of the medical robot 10 rather than to the end of an articulated arm 14.

By way of nonlimiting example, in the remainder of the description a tool 15 is mounted at the end of an articulated arm 14 of the medical robot 10.

It is important for the arm 14 of the medical robot 10 to be able to position the tool 15 as accurately as possible at a predetermined position or to move the tool 15 as accurately as possible in a predetermined space or in accordance with a predetermined trajectory. To this end, it is necessary to identify an optimum position of the mobile base 13 of the medical robot 10 at which the articulated arm 14 of the medical robot 10 will be able to effect the required movements during the treatment.

The mobile base 13 may advantageously incorporate a mechanism for immobilizing the medical robot 10. There is then provision for activating this immobilization mechanism before carrying out the medical treatment, once the medical robot 10 is positioned at an optimum position relative to the position of the patient 30, in order to immobilize the mobile base 13 of the medical robot 10 at said optimum position. This in particular enables stabilization of the medical robot 10 during movements of the arm 14 during the treatment.

The quality of the stabilization of the medical robot 10 is an important element for the accuracy and the efficacy of the actions effected by the medical robot 10 during a medical treatment. However, it is not an essential element for the positioning of the medical robot 10.

Figure 2:
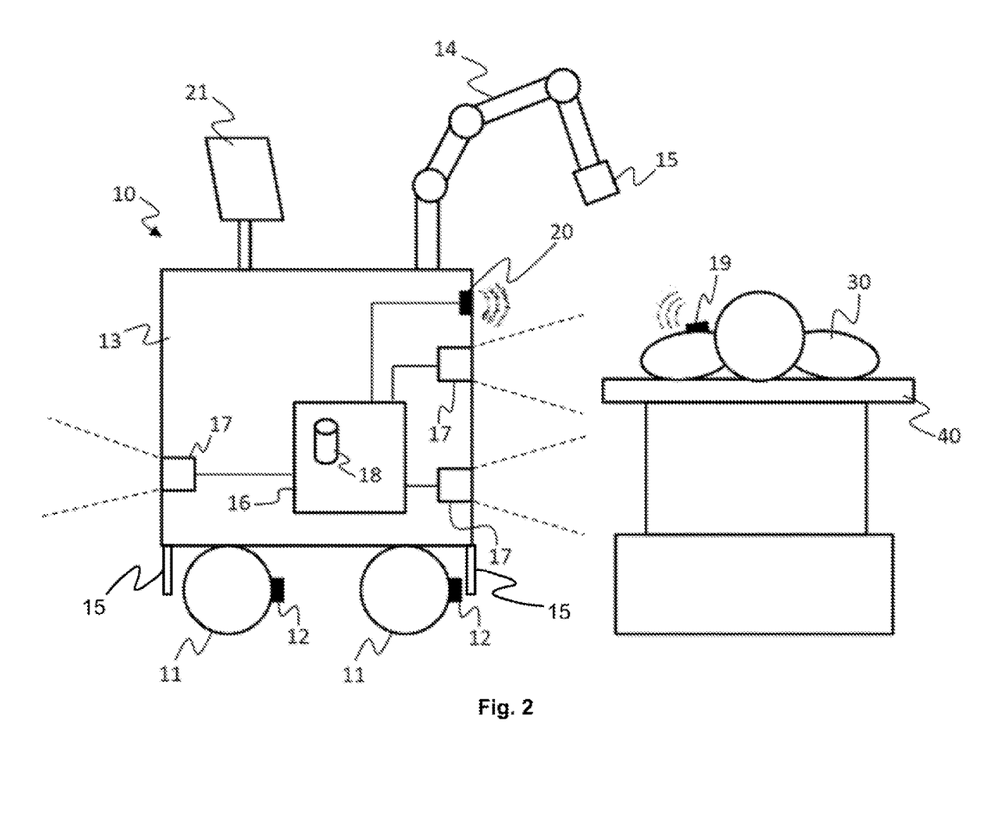
FIG. 2: a detailed diagrammatic representation of a medical robot according to the invention.

The immobilization mechanism may take a number of forms. For example, and as represented in FIG. 2, a brake 12 may be associated with each wheel 11 of the mobile base 13. Each brake 12 may for example be conventionally controlled by pneumatic, hydraulic or electrical means.

In particular embodiments stabilizers taking the form of retractable feet associated with hydraulic or electrical cylinders for lowering them into contact with the floor are provided to support all or part of the weight of the medical robot 10.

The medical robot 10 is configured to identify autonomously, as a function of the position of an anatomy of interest of the patient 30 and of a treatment plan, at least one favourable position of the mobile base 13 of the medical robot 10 at which the medical robot 10 will be able to execute the intended treatment actions.

By "anatomy of interest" of the patient is meant at least a part of the human body of the patient 30 to which the medical treatment must be applied.

An optimum position of the mobile base 13 of the medical robot 10 for the treatment is then selected from the identified favourable position or positions. The medical robot 10 is configured to move autonomously to said optimum position.

It may be advantageous for the medical robot 10 to detect the position of the table 40 and to identify the favourable position or positions as a function of the position of the table 40. A treatment table is in fact an object that can be recognized by a shape recognition algorithm. Moreover, when the patient is placed on a table 40, which is the case in most situations in which a patient has to undergo a medical treatment, determining a favourable position of the mobile base 13 of the medical robot 10 must take into account the overall size of the table 40.

However, it must be noted that the identification of the position of a treatment table is not indispensable to positioning the medical robot. In fact, in some cases the patient is not necessarily placed on a treatment table, as for example when the medical robot is used to produce medical images of a patient standing in a treatment room.

It is considered by way of nonlimiting example in the remainder of the description that the medical robot 10 detects the position of the table 40 and uses that information to identify a favourable position of the mobile base 13.

As shown in FIG. 2 the medical robot 10 includes spatial location sensors 17 fastened to the mobile base 13.

These spatial location sensors 17 may be video cameras, for example: basic video cameras, stereoscopic video cameras, panoramic video cameras, video cameras mounted on a telescopic boom, video cameras effecting rotations of 360°, video cameras operating in accordance with the time of flight (ToF) principle, so-called RGB-D depth video cameras (supplying simultaneously a colour image and a depth map characterizing the distance of the object seen in the image), etc. Of course, these different features of cameras may be combined with each other when technically possible (for example an RGB-D camera mounted on a telescopic boom and adapted to effect a rotation of 360°).

These spatial location sensors 17 may equally be rangefinders for measuring the distance to the various elements of the environment: ultrasound rangefinders, infrared rangefinders, laser rangefinders, etc.

They may equally be proprioceptive sensors enabling measurement of the movement of the mobile base 13: odometric sensors, measuring the movement of the wheels with an optical encoder, optical sensors measuring the relative movement with respect to the floor, inertial systems using accelerometers and rate gyros, etc.

These spatial location sensors 17 are known to the person skilled in the art. They make it possible, on the one hand, to locate objects in space, for example using shape recognition methods. They make it possible, on the other hand, to estimate the distances between different objects. They also enable the medical robot 10 to estimate its position as well as the distance travelled when the medical robot 10 moves.

When the medical robot 10 is introduced into a treatment room 50 the data supplied by the various spatial location sensors 17 in particular enables detection of the treatment table 40 and the patient 30 placed on said table and estimation of the positions of the table 40 and of the anatomy of interest of the patient 30 relative to the medical robot 10. The positions of the table 40, of the patient 30 and of the medical robot 10 may be defined in the same spatial frame of reference, for example a three-dimensional frame of reference.

In particular, it is possible to associate images from an RGB-D video camera with medical images by surface matching in order accurately to detect and to locate an anatomy of interest of the patient 30. To establish the correspondence between the images from the RGB-D video camera and the frame of reference of the medical robot 10, there are at least two known techniques. A first technique consists for example in ensuring that the imaging by the RGB-D video camera is such that distinctive geometric elements of the arm 14 of the medical robot 10 are present in the images from the RGB-D video camera in order to locate both the medical robot 10 and the anatomy of interest of the patient 30. A second technique consists in first calibrating the position of the RGB-D video camera on the medical robot 10.

In particular embodiments one or more markers 19 may be positioned on the anatomy of interest of the patient 30. Those markers 19 cooperate with sensors 20 of the medical robot 10 in order to assist detection and location of the position of the anatomy of interest of the patient 30. For example, a passive light-reflecting marker 19 or an active marker 19 that includes a light-emitting diode can be detected by a specific sensor 20. According to another example, an electromagnetic marker 19 can emit a radio signal that can be picked up by a sensor 20 on board the medical robot 10. The time taken by a radio signal or a light signal emitted by a sensor 20 and returned by a marker 19 can for example make it possible to determine the distance between the marker 19 and the sensor 20 in order to deduce therefrom the position and/or the orientation of the anatomy of interest of the patient 30. The sensors 20 are carried by the medical robot 10, that is to say are fastened to the mobile base 13 of the medical robot 10.

The data provided by the spatial location sensors 17 and the sensors 20 for aiding detection of the anatomy of interest of the patient 30 then enable detection of the position of the medical robot 10, the position of the table 40 and the position of the anatomy of interest of the patient 30 defined relative to one another in the same spatial frame of reference.

This data is communicated to a control unit 16 of the medical robot 10. The control unit 16 includes for example one or more processors and a memory 18 (magnetic hard disk, electronic memory, optical disk, etc.) in which is stored a computer program product in the form of a set of program code instructions to be executed to implement the various steps of a method for automatic positioning of the medical robot 10 in a treatment room 50. Alternatively or additionally the control device includes one or more programmable logic circuits (FPGA, PLD, etc.) and/or one or more application-specific integrated circuits (ASIC) and/or discrete electronic components, etc., adapted to implement all or part of said steps of said positioning method.

Data from the sensors 17, 20 of the medical robot can be communicated to the control unit 16 in the conventional manner by computer buses including electrical wires or by wireless communication systems.

The control unit 16 is configured with the aid of algorithms using the data from the sensors 17, 20 of the medical robot 10 to detect the positions of the table 40 and of the anatomy of interest of the patient 30 relative to the position of the medical robot 10 and then, with the aid of those positions, to identify at least one favourable position of the mobile base 13 of the medical robot 10 at which the medical robot 10 is able to carry out the treatment plan.

An optimum position of the mobile base 13 of the medical robot 10 is then selected from all the identified favourable positions.

The control unit 16 is also configured to control the motorized mobile base 13 of the medical robot 10. The control unit 16 can then move the medical robot 10 to the selected optimum position.

Once the mobile base 13 of the medical robot 10 has reached said optimum position the control unit 16 can trigger a mechanism for immobilizing the mobile base 13 in order to ensure stabilization of the medical robot 10 during the treatment.

In particular embodiments, the control unit 16 is furthermore configured to trigger the immobilization of the mobile base 13 of the medical robot 10 in the optimum position selected only if a stability criterion is verified. If this is not the case, the control unit 16 may be configured to move the mobile base of the medical robot to another position selected from the favourable positions. These steps may be repeated until a favourable position is selected for which the stability criterion is verified. If there is no position among the identified favourable positions for which the stability criterion is verified, then a warning message may be sent via a user interface 21 of the medical robot 10.

The medical robot comprises, for example, retractable feet 15 intended to be lowered to immobilize the mobile base of the medical robot. One example of retractable feet usable with aspects of the disclosure are described in French priority Application No. FR190215A, which has been incorporated by reference herein. For example, each foot comprises a part suspended on the mobile base 13 of the medical robot 10 and a bearing part in sliding relationship with the suspended part. The bearing part comprises a base of the foot intended to rest on the surface of the floor when the foot is in a bearing position. When the medical robot 10 is not immobilized, the feet 15 occupy a retracted position and are not in contact with the surface of the floor.

According to a first example, each foot comprises a sensor making it possible to measure a local flatness defect of the floor facing said foot. In order to verify the stability criterion, the control unit 16 can then compare, for each foot, the measurement of the local flatness defect of the floor for said foot with a predetermined threshold. If the local flatness defect of the floor for one of the feet 15 is greater than the threshold, then the stability criterion is not satisfied. The sensor for measuring a local flatness defect of the floor is adapted to determine if there is an offset between the position of the floor facing each foot relative to a predefined theoretical position of the floor. This offset corresponds to a local flatness defect of the floor. The measuring sensor may be, for example, an ultrasound sensor, the operation of which is known as such to the person skilled in the art. Each ultrasound sensor may be fixed into the base of a foot of the medical robot 10 and directed so as to measure the distance between said base and the surface of the floor that it faces. The measurement is carried out when the foot is in a retracted position for which the distance between die base of the foot and the surface of the floor, in a theoretical case of absence of a local flatness defect of the floor, is known.

According to a second example, on each foot a compression cod spring is used in combination with the sliding of the suspended part relative to the bearing part so that said foot supports only part of the weight of the medical robot 10 when the latter is immobilized. Thanks to the mobility of the suspended part relative to the bearing part and to the cod spring, each toot locally compensates any local flatness defects of the floor, of hollow or bump type, so that the mobile base 13 of the medical robot 10 is supported in a substantially horizontal manner and all of the feet 15 bear on the floor despite possible local flatness defects. This allows the stability of the medical robot 10 to be assured. In other words, for each foot, the bearing part will slide more or less along the length of the suspended part, and the coil spring will be more or less compressed, depending on whether it has to compensate hollow or a bump. Each foot comprises a sensor making it possible to measure a weight supported by said foot. This is, for example, a force sensor making it possible to measure the compression of the coil spring. In order to verify the stability criterion, the control unit 16 can then compare, for each foot, the measurement of the weight supported by said foot with a predetermined threshold. If the weight supported by one of the feet 15 is greater than a threshold corresponding to the maximum weight which can be supported by each foot (or less than a threshold corresponding to a minimum weight which must be supported by each foot), then the stability criterion is not satisfied. It should be noted that the favourable positions of the mobile base 13 of the medical robot 10 may be identified after one or more intermediate steps of movement of the medical robot 10. For example, the medical robot 10 may first move toward the table 40 to identify more precisely the position of the anatomy of interest of the patient 30 before identifying favourable positions of the mobile base 13 for the treatment.

The favourable positions of the mobile base 13 of the medical robot 10 for the treatment are identified not only as a function of the position of the table 40 and of the position of the anatomy of interest of the patient 30, but also as a function of the treatment plan stored in the memory 18 of the control unit 16.

The treatment plan includes one or more actions to be carried out on the anatomy of interest of the patient 30. One action from the treatment plan corresponds for example to being able to manipulate the tool 15 in a predetermined space, to placing the tool 15 in a predetermined position, or to moving the tool 15 along a predetermined trajectory relative to the anatomy of interest of the patient 30. According to another example, one action from the treatment plan may equally consist in having the tool 15 execute a particular operation, such as for example starting up an ultrasound generator or modifying the intensity of ultrasound emission, or triggering the capture of a medical image.

The treatment plan is created during a planning phase that precedes the medical treatment. During this planning phase the practitioner defines the various actions that the medical robot 10 has to effect.

The treatment plan may for example be generated with the aid of medical images of CT (computerized tomography) scanner, MRI, PET, ultrasound, X-ray, etc type. An operator, generally the practitioner who will carry out the treatment with the aid of the medical robot 10, selects the parameters of the tool 15 (for example a length, a diameter, a 3D shape, a power to be delivered, a current, a treatment time, etc.). One or more trajectories may be planned according to the type of treatment to be effected to destroy the tumour. The planning may be completely manual, interactive or completely automated with the aid of segmentation and planning algorithms. The decision-aid algorithms may for example be based on expert systems (systems capable of reproducing the cognitive mechanisms of the practitioner through reasoning based on facts and known rules) or on intelligent automatic learning mechanisms (for example using convolutive neural networks).

Alternatively or additionally the treatment may be planned without medical images thanks to a three-dimensional representation of the anatomy of interest to be treated. This three-dimensional representation may be obtained by a non-medical image acquisition system or by collecting anatomical surfaces or markers and interpolation of a statistical or biomechanical model of those markers or surfaces. This type of planning is particularly effective in treatment of bone structures such as joints (knee, hip, shoulder, etc.) for example.

The actions from the treatment plan are for example encoded in a computer file in the form of instructions known by the control unit 16. The computer file corresponding to the treatment plan may for example be generated on a computer separate from the medical robot 10. The file is then transmitted to the medical robot 10 and stored in the memory 18 of the control unit 16. This transmission of the computer file may take various conventional forms, such as for example file transmission by USB (Universal Serial Bus) key, or by wireless communication.

The actions from the treatment plan describe for example the various positions or the various movements of the tool 15 relative to the anatomy of interest of the patient 30. The control unit 16 moreover knows the geometrical model of the articulated arm 14 and of the tool 15. For example, the arm 14 is equipped with encoders enabling knowledge of the angular position of each of its axes and, by calculation, the position of the tool 15. The control unit 16 is then able to determine one or more favourable positions of the mobile base 13 at which the medical robot 10 will be able to perform the gestures provided by the treatment plan.

One action from the treatment plan is an action that the medical robot will have to execute during the treatment, subsequently to the process of automatic positioning of the medical robot. The execution of an action of this kind is therefore not part of the method according to the invention for automatic positioning of the medical robot.

In one particular embodiment a favourable position identification algorithm consists for example in discretizing the space of the possible positions of the medical robot 10 relative to the anatomy of interest of the patient 30 and in defining an accessibility parameter representing a number of possible configurations of the articulated arm 14 enabling an action from the treatment plan to be effected when the mobile base 13 of the medical robot 10 is positioned at a given position. the articulated arm 14 includes one or more articulations controlled by the control unit 16. One possible configuration of the articulated arm then corresponds to a set of values of parameters taken by the articulation or articulations of the arm (for example an angle of rotation, a distance in translation, etc.).

By "possible position" is meant a position of the mobile base 13 of the medical robot 10 at which the articulated arm 14 can reach the anatomy of interest of the patient. The set of possible positions therefore corresponds to a working space in which the anatomy of interest of the patient is within reach of the articulated arm 14.

For an articulated arm 14 of the medical robot 10 having more degrees of freedom than necessary to effect a planned action, a plurality of configurations of the arm 14 may be envisaged. For example, the articulated arm 14 of an anthropomorphic medical robot 10 with six degrees of freedom is generally able to position a needle-guide in a rectilinear direction passing through a predetermined entry point in accordance with a plurality of different configurations of its axes. If only one configuration is possible the accessibility parameter will be of lower value than if two different configurations are possible.

In the example considered here a favourable position corresponds to a position of the mobile base 13 of the medical robot 10 at which there exists, for each action from the treatment plan, at least one configuration of the articulated arm 14 enabling said action to be effected.

The difference between "possible position" and "favourable position" should be noted: if the anatomy of interest is accessible by the articulated arm 14 at a given position of the mobile base 13, that does not necessarily mean that there is a configuration of the articulated arm 14 for carrying out each action from the treatment plan if the mobile base 13 is positioned at that position.

The accessibility parameter may equally be defined as a function of representative values of available relative movements of the articulations of the arm 14 for the various possible configurations of said arm 14 enabling an action from the treatment plan to be effected at a given favourable position. The relative movement of an articulation is for example limited by one or more abutments. By "available relative movement" of an articulation is meant a representative parameter of the amplitude of a movement permitted by said articulation, such as for example an angle between the position of a segment of the articulation for a given configuration and the nearest abutment.

A global level of accessibility can then be calculated for each identified favourable position as a function of the accessibility parameters of all the actions from the treatment plan. For example a global level of accessibility for an identified favourable position may correspond to the sum of the accessibility parameters of all the actions from the treatment plan when the mobile base 13 of the medical robot 10 is positioned at said favourable position. There are of course other methods for calculating a global level of accessibility. For example, weightings may be applied as a function of the importance of an action relative to other actions from the treatment plan.

The control unit 16 can then be configured to select an optimum position from all of the identified favourable positions as a function of the accessibility parameters or of the global level of accessibility calculated for the various identified favourable positions. For example, the optimum position may correspond to the favourable position for which the accessibility parameter of a particular action from the treatment plan has the greatest value. According to another example, the optimum position may correspond to the favourable position for which the global level of accessibility has the greatest value.

Such features enable greater flexibility during the treatment. In fact the practitioner could, once the robot is positioned at the optimum position, chose, during the treatment, between a plurality of possible configurations for effecting such or such an action from the treatment plan. The preference for one particular configuration over another could depend on the progress of the treatment.

In particular embodiments the control unit 16 uses algorithms to calculate the optimum position taking account of information from a database of medical treatments already carried out: real position of the medical robot 10 relative to the anatomy of interest of the patient 30, accessibility parameters of planned and completed actions, positions and movements of the tool 15 inaccessible during the treatment, etc.

These algorithms may be based on known automatic learning methods (learning by neural networks, supervised automatic learning, semi-supervised or unsupervised automatic learning, etc.). These algorithms are advantageous because instead of proposing theoretical optimum positions they are able to propose optimum positions taking into account the reality of treatments already carried out, the latter positions possibly being significantly different from the former as a function of the complexity of the theoretical modelling of the problem of positioning the mobile base 13 relative to the anatomy of interest of the patient 30. The control unit 16 can be configured to store, during a medical treatment, information on the position of the medical robot 10 relative to the anatomy of interest of the patient 30 and on accessibility parameters so that this data can be used again afterwards by artificial intelligence algorithms to optimize the positioning of the medical robot 10 during a future treatment.

Training data, corresponding to the information relating to treatments already carried out, such as the planned actions that necessitate positions of the tool 15 relative to the patient 30, the real position of the mobile base 13 of the medical robot 10 relative to the patient 30 during the treatment, the positions reached, the inaccessible positions, the available relative movements and other movements, are for example stored in the memory 18 of the control unit 16. A processor of the control unit 16 is then able to create a multilayer neural network depth model based on the training data. That model is stored in the memory 18 of the control unit 16. During new treatments the learned neural network model is applied to the planned actions and participates in determining the optimum position for executing the treatment plan.

In particular embodiments preferences of a practitioner can be stored in the memory 18 of the control unit 16 and taken into account when selecting the optimum position of the medical robot 10. The preferences may take into account for example the intended position of the patient 30 on the table 40 of the treatment room 50 (dorsal, ventral, lateral decubitus), whether the practitioner is left-handed or right-handed, a preferred side of the table 40 for installing the robot, etc.

In particular embodiments, the medical robot 10 includes a user interface 21 enabling the medical robot 10 to present information to the practitioner and a command to be given to the medical robot 10. That user interface 21 includes for example a screen, a keyboard, a mouse, a button, a joystick, a touch screen, a voice or gesture recognition system, or any other means enabling the medical robot 10 to present information to the practitioner and to receive from the practitioner a signal associated with a known command. For example, rather than selecting the optimum position autonomously, the medical robot 10 can show all of the identified favourable positions on a screen and leave it to the practitioner to chose the optimum position from all of those favourable positions. According to another example, during the treatment, if a plurality of configurations of the articulated arm 14 are possible for effecting an action from the treatment plan, those different configurations may be presented on a screen in order for the practitioner to chose the preferred configuration.

In particular embodiments the user interface 21 furnishes an indication to the practitioner that the medical robot 10 has reached the optimum position and the practitioner can validate that position and trigger immobilization of the mobile base 13 at said optimum position.

In a variant, the control unit 16 autonomously triggers immobilization of the mobile base 13 when the medical robot 10 has reached the optimum position.

In particular embodiments, the medical robot 10 generates a mapping of the treatment room 50 to determine the optimum position to be reached.

Figure 3:
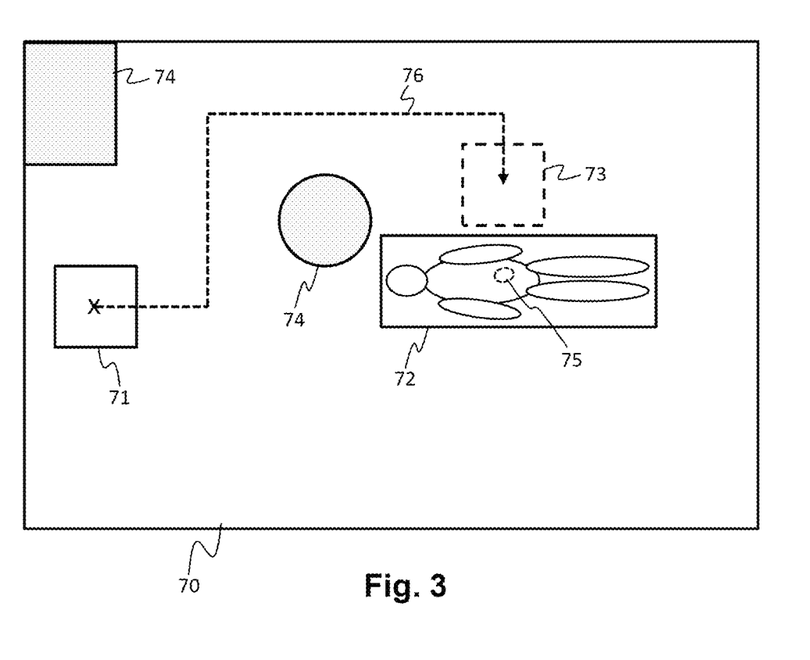
FIG. 3: a diagrammatic representation of a mapping of a treatment room generated by the medical robot and a path to be taken to reach an optimum position for treating the patient.

FIG. 3 represents diagrammatically a mapping 70 of the treatment room 50 and a path 76 of the medical robot 10 to reach an optimum position 73 for treating the patient 30.

It should be noted that FIG. 3 represents diagrammatically a two-dimensional mapping 70, as seen from above, but there is nothing to prevent said mapping 70 from being produced in three dimensions. A three-dimensional mapping advantageously enables better account to be taken of the overall size of the various elements present in the treatment room 40.

During the process of automatic positioning of the medical robot 10, once the patient 30 has been placed in the treatment room 50, the mapping 70 is produced for example by the control unit 16 of the medical robot 10. The mapping 70 is for example produced with the aid of a spatial location sensor 17 of RGB-D video camera type mounted on a telescopic boom fixed to the mobile base 13 and with the aid of a shape recognition algorithm. The control unit 16 then determines on the mapping 70 the position 71 of the robot, the position 72 of the table 40, the position 75 of the anatomy of interest to be treated, and the positions 74 of any obstacles that could impede the movements of the medical robot 10.

The control unit 16 is configured to identify, as a function of the position 71 of the medical robot 10, of the position 72 of the table 40, of the position 75 of the anatomy of interest of the patient 30 and of the stored treatment plan, at least one favourable position at which the treatment plan can be executed by the medical robot 10. An optimum position 73 is then selected and a path 76 is determined by the control unit 16 so that the medical robot 10 can reach the optimum position 73 taking account of the positions 74 of any obstacles in order to avoid them.

It should be noted that intermediate movements may be effected by the medical robot 10, for example to move toward the table 40, before determining the precise optimum position 73.

The mobile base 13 may incorporate shock absorbers to minimize damage in the event of a collision. Those shock absorbers may be combined with touch-sensitive sensors enabling the movement of the mobile base 13 to be stopped automatically in the event of contact with an obstacle. Alternatively or additionally the movement of the medical robot 10 may be stopped manually, for example using an emergency button.

The motorized assistance of the mobile base 13 and the spatial location sensors 17 of the medical robot 10 may equally be used in the context of a method for transferring the medical robot 10 from a storage zone of the medical robot 10 to the treatment room 50 and vice-versa. This kind of method for transferring the medical robot 10 is executed before and/or after automatically positioning the medical robot.

The medical robot 10 may be transferred from its storage zone to the treatment room 50 autonomously by the medical robot 10 or with the assistance of an operator.

When the medical robot 10 is in its storage zone, it is able to go to the treatment room 50 by following an operator located in front of or behind the mobile base 13 with the aid of the spatial location sensors 17 and control means implemented by the control unit 16 (module for detecting the relative position of the operator, movement setpoint module, guide module, obstacle detection module, etc.).

The mobile base 13 can also incorporate one or more video cameras at the front and on the sides in order to transmit to a screen images of the environment around the medical robot 10 enabling the operator located behind the mobile base 13 to be located better and to facilitate movement in a corridor, going through a door, or avoiding obstacles.

When the mobile base 13 is in its storage zone it is able to go to a treatment room 50 in an entirely autonomous manner if the various rooms of the building in which it is located have been mapped beforehand. In this case, during a previous step, information concerning the location of the storage zone and that of the treatment room 50 are indicated to the medical robot 10. the access doors to these various zones are for example fitted with sensors or QR (Quick Response) codes enabling the medical robot 10 to detect said access doors and said access doors to authorize the passage of the medical robot 10.

Once the medical robot 10 is in the treatment room 50 it can then be positioned automatically at an optimum position 73 for the treatment.

Figure 4:
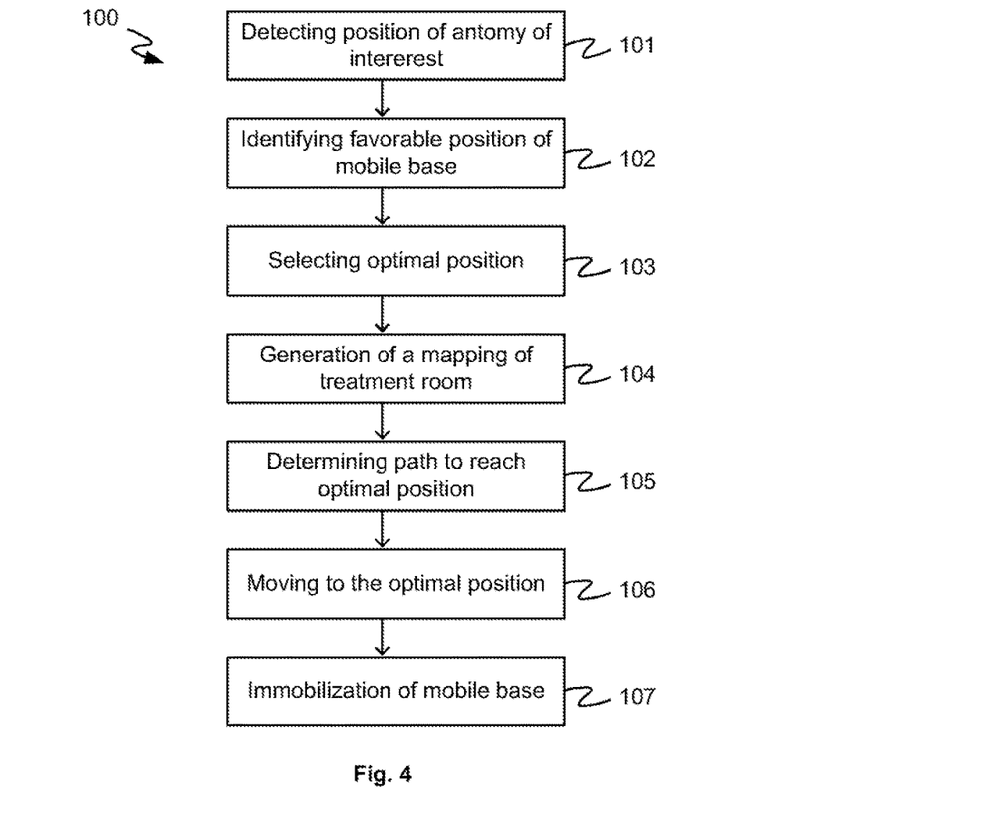
FIG. 4: the main steps of a particular embodiment of a method according to the invention for automatic positioning of a medical robot.

FIG. 4 represents diagrammatically the main steps of a method 100 according to the invention for automatic positioning of a medical robot 10 as described with reference to FIGS. 1 to 3.

The automatic positioning method 100 is executed by the control unit 16 of the medical robot 10.

The method 100 of automatic positioning of the medical robot 10 commences when it enters the treatment room 50 at the start of the medical treatment. The patient 30 is then placed on a table 40 in the treatment room 50.

The method 100 includes a step 101 of detecting the position 75 of the anatomy of interest of the patient 30 relative to a position 71 of the medical robot 10. In the example considered, the position 72 of the table 40 is also detected in this step. This step is carried out autonomously by the medical robot 10.

The method 100 also includes a step 102 of identifying from the position 75 of the anatomy of interest of the patient 30 and the treatment plan at least one favourable position of the mobile base 13 of the medical robot 10 at which the medical robot 10 is able to effect the actions from the treatment plan. In the example considered, this identification step 102 is furthermore based on the position 72 of the table 40. This step is executed autonomously by the medical robot 10.

An optimum position 73 is then selected 103 from all the favourable positions. As explained above, the selection 103 of the optimum position 73 may be effected as a function of the accessibility parameters or of a global level of accessibility calculated for each favourable position as a function of stored preferences and/or with the aid of information extracted from a database of medical treatments already carried out. This selection 103 may be carried out by the practitioner to whom the various favourable positions are shown on a user interface 21.

The positioning method 100 may optionally include generation 104 of a mapping 70 of the treatment room 50 on which are represented a position 71 of the medical robot 10, the position 72 of the table 40, the position 75 of the anatomy of interest of the patient 30, and the optimum position 73 to be reached, together with determination 105, on the basis of said mapping 70, of a path 76 of the medical robot 10 to reach said optimum position 73.

The method 100 includes a step 106 of the medical robot 10 moving to the optimum position 73. This movement 106 is effected autonomously by the medical robot 10.

It should be noted that the order of the above steps is not necessarily fixed. Also, one or more intermediate steps of movement of the medical robot 10 in the direction of the table 40 may take place before the medical robot 10 is in a position to detect the anatomy of interest of the patient 30 and to identify favourable positions for carrying out the treatment.

It is also important to note that no mapping need be supplied to the medical robot 10. Thus the medical robot 10 may initially have no mapping of the treatment room 50 at the start of the automatic positioning process 100.

The method for automatic positioning of the medical robot 10 may advantageously include a step 107 of immobilization of the mobile base 13 when the optimum position 73 has been reached. This immobilization step 107 may be executed autonomously by the medical robot 10 or with the participation of an operator. For example, the immobilization step 107 may be triggered by a command from the practitioner after validating the optimum position reached on the user interface 21.

As explained above, the immobilization of the mobile base of the medical robot in the optimum position can only be triggered if a stability criterion of the mobile base of the medical robot is verified. If this is not the case, the automatic positioning method according to the invention may comprise an additional step of moving the mobile base of the medical robot to another position selected from the favourable positions.

Figure 5:
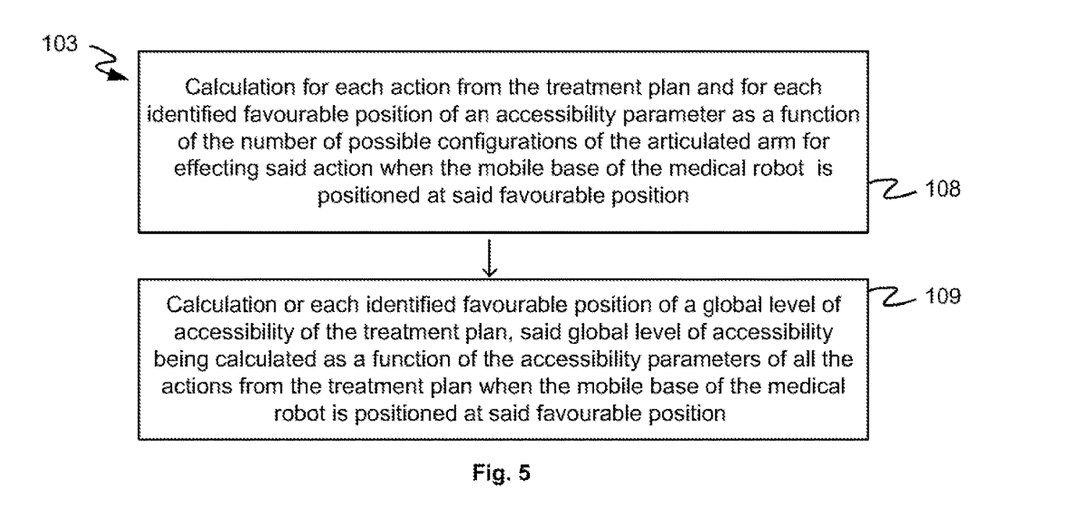
FIG. 5: the main steps of a particular way of selecting an optimum position of a medical robot from a plurality of favourable positions.

In the example considered, the medical robot 10 includes an articulated arm 14 and a tool 15 mounted at one end of said arm 14. The arm 14 is configured by the control unit 16 of the medical robot 10 to effect an action from the treatment plan. As shown in FIG. 5, the selection 103 of the optimum position 73 may then include:

calculation 108 for each action from the treatment plan and for each identified favourable position of an accessibility parameter as a function of the number of possible configurations of the articulated arm 14 for effecting said action when the mobile base 13 of the medical robot 10 is positioned at said favourable position, calculation 109 for each identified favourable position of a global level of accessibility of the treatment plan, said global level of accessibility being calculated as a function of the accessibility parameters of all the actions from the treatment plan when the mobile base 13 of the medical robot 10 is positioned at said favourable position.

It should be noted that the calculation 108 of the accessibility parameter may also be effected as a function of representative values of the available relative movements of the articulations of the arm 14 for the various possible configurations of the arm 14 enabling an action from the treatment plan to be effected at a given favourable position.

The foregoing description shows clearly that, through its various features and their advantages, the present invention achieves the set objectives. In particular, it proposes a solution for facilitating and making reliable the automatic positioning of a medical robot 10 in a treatment room 50.

The steps of the positioning method 100 according to the invention are mostly executed autonomously by the medical robot 10, which eliminates positioning errors linked to the intervention of an operator or of an additional device used to control the robot. Also, the absence of an additional device separate from the medical robot 10 limits the maintenance load of a robot-based medical treatment assistance system.

Also, the medical robot 10 according to the invention is able to adapt to the real position of the anatomy of interest of the patient 30 at the time of the treatment, the latter anatomy possibly differing significantly from an anatomy modelled during a planning phase.

Also, the medical robot 10 can be positioned automatically in any treatment room 50, even if the medical robot 10 has no mapping or specific information relating to the layout of the room 50 before the method for automatic positioning of the medical robot 10 commences. This then limits the maintenance costs and loads relative to the medical treatments assisted by a medical robot.

The invention claimed is:

1. A method for automatic positioning of a medical robot carry out a medical treatment on a patient, said medical robot including a motorized mobile base enabling movement of the medical robot and a control unit storing a treatment plan including at least one action to be effected on an anatomy of interest of said patient, said positioning method comprising following steps executed autonomously by the medical robot:

detecting the position of the anatomy of interest of the patient relative to a position of the medical robot,  identifying on the basis of the position of the anatomy of interest of the patient and of the treatment plan of at least one favorable position of the mobile base of the medical robot at which the medical robot is capable of effecting said at least one action from the treatment plan, and  moving the mobile base of the medical robot to an optimum position selected from the identified favorable position or positions,  verifying a stability criterion of the mobile base of the medical robot in the selected optimum position,   if said verification is positive, immobilizing the mobile base of the medical robot in said optimum position,   if said verification is negative, moving the mobile base of the medical robot to another position selected from the favorable positions, wherein the medical robot comprises retractable feet intended to be lowered to immobilize the mobile base of the medical robot, each foot comprising:

a sensor to measure a local flatness defect of a floor facing said foot, and the verification of a stability criterion comprises, for each foot, a comparison of the measurement of the local flatness defect of the floor for said foot with a predetermined threshold,   a second sensor for measuring a weight supported by said foot, and the verification of a stability criterion comprises, for each foot, a comparison of the measurement of the weight supported by said foot with a predetermined threshold.

2. The method of claim 1, wherein the patient is installed on a table of treatment room, the method further comprising detecting the position of the table and identifying at least one favorable position of the mobile base of the medical robot on the basis of the position of the table.

3. The method of claim 2, wherein the detection of the position of the table and the detection of the anatomy of interest of the patient are effected on the basis of information from spatial location sensors carried by the medical robot.

4. The method of claim 3, wherein the robot initially has no mapping of the treatment room.

5. The method of claim 4, further comprising the following steps executed autonomously by the medical robot:

generating a mapping of the treatment room on which are represented a position of the medical robot, the position of the table, the position of the anatomy of interest of the patient, and the optimum position,  determining the basis of said mapping of a path of the medical robot to reach said optimum position.

6. The method of claim 1, wherein the medical robot comprises an articulated arm and a tool mounted at one end of said arm, one or more articulations of said arm being controlled by the control unit of the medical robot to position the arm in accordance with one possible configuration, a favorable position corresponds to a position of the mobile base of the medical robot at which there exists for each action from the treatment plan at least one possible configuration of the articulated arm enabling said action to be effected, the method further comprises calculating each action from the treatment plan and each identified favorable position of an accessibility parameter as a function of a number of possible configurations of the articulated arm for effecting said action when the mobile base of the medical robot is positioned at said favorable position, wherein the optimum position is selected as a function of the accessibility parameters of the identified favorable positions.

7. The method of claim 6, wherein said accessibility parameter is furthermore calculated as a function of available relative movements of the articulations of the arm for of said possible configurations of the arm.

8. The method of claim 6, wherein the method further comprises calculating each identified favorable position of a global level of accessibility of the treatment plan, said global level of accessibility being calculated as a function of the accessibility parameters of each action from the treatment plan when the mobile base of the medical robot is positioned at said favorable position, wherein the optimum position is selected as a function of the global levels of accessibility calculated for the identified favorable positions.

9. The method of claim 6, wherein one action from the treatment plan corresponds to enabling the movement of the tool in a predetermined volume relative to said anatomy of interest of the patient.

10. The method of claim 6, wherein one action from the treatment plan corresponds to enabling movement of the tool with a predetermined trajectory relative to said anatomy of interest of the patient.

11. The method of claim 6, wherein sine action from the treatment plan corresponds to placing the tool in a predetermined position relative to said anatomy of interest of the patient.

12. The method of claim 1, wherein the optimum position is selected as a function of preferences of an operator stored in the control unit.

13. The method of claim 1, wherein the optimum position is selected by an automatic learning algorithm as a function of information extracted from an existing medical treatment database.

14. The method of claim 13, wherein said automatic learning algorithm uses a multilayer network.

15. The method of claim 1, wherein the medical robot includes a user interface, the identified Favorable positions are proposed to an operator via said user interface, and the optimum position is selected by said operator.

16. A medical robot: comprising a motorized mobile base, spatial location sensors fastened to the mobile base, and a control unit storing a treatment plan including at least one action to be carried out on an anatomy of interest of a patient, wherein said control unit is configured:

to detect on the basis of information from the spatial location sensors a position of the anatomy of interest of the patient relative to the medical robot,  to identify on the basis of the position of the anatomy of interest of the patient and of the treatment plan at least one favorable position of the mobile base of the medical robot at which the medical robot is capable of effecting said at least one action from the treatment plan, and  to move the mobile base of the medical robot to an optimum position selected from the identified favorable position or positions, to verify a stability criterion of the mobile base of the medical robot hi the selected optimum position, if said verification is positive, to trier an immobilization of the mobile base of the medical robot in said optimum position, if said verification is negative, to move the mobile base of the medical robot to another position selected from the favorable positions, wherein the medical robot comprises retractable feet intended to be lowered to immobilize the mobile base of the medical robot, each foot comprising:

a sensor making it possible to measure a local flatness defect of a floor facing said foot, and, in order to verify the stability criterion, the control unit compares, for each foot, the measurement of the local flatness defect of the floor for said foot with a predetermined threshold, a sensor making possible to measure a weight supported by said foot, and, in order to verify the stability criterion, the control unit compares for each foot, the measurement of the weight supported by said foot with a predetermined threshold.

17. The medical robot of claim 16, wherein the control unit is also configured to detect on the basis of information from the spatial location sensors a position of a table of a treatment room on which the patient (30) is placed and to identify said at least one favorable position as a function of the position of the table.

18. The medical robot of claim 17, wherein the control unit is also configured:

to generate a mapping of the treatment room on which are represented a position of the medical robot, the position of the table, the position of die anatomy of interest of the patient, and the optimum position, to determine on the basis of said mapping a path of the medical robot to reach said optimum position.

19. The medical robot of claim 16, wherein the medical robot comprises sensors to assist detection of the anatomy of interest of the patient cooperating with markers positioned on said anatomy of interest, the sensors aiding detection of the anatomy of interest of the patient being fastened to the mobile base of the medical robot.

20. The medical robot of claim 16, wherein the information from sensors used to identify the favorable position or positions are furnished exclusively by sensors carried by the medical robot.

21. The medical robot of claim 18, further comprising an articulated arm and a tool mounted at one end of said arm, one or more articulations of said arm being controlled by the control unit of the medical robot to position the arm in accordance with one possible configuration, a favorable position corresponding to a position of the mobile base of the medical robot at which there exists for each action from the treatment plan at least one possible configuration of the articulated arm enabling said action to be effected and the control unit is further configured:

to calculate for each action from the treatment plan and for each identified favorable position an accessibility parameter representing a number of possible configurations of the articulated arm for effecting said action when the mobile base of the medical robot is positioned at said favorable position, and to select the optimum position as a function of the accessibility parameters of the identified favorable positions.

* * * * *